(12) United States Patent
Averkiou et al.

(10) Patent No.: US 6,171,246 B1
(45) Date of Patent: Jan. 9, 2001

(54) REALTIME ULTRASONIC IMAGING OF PERFUSION USING ULTRASONIC CONTRAST AGENTS

(76) Inventors: Michalakis Averkiou, 11023 115th Ct. NE. #E106, Kirkland, WA (US) 98033; Jeffry E. Powers, 4054 W. Blakely Ave. NE., Bainbridge Is., WA (US) 98110; Matthew Bruce, 4215 12th Ave. #1, Seattle, WA (US) 98105; Danny M. Skyba, 22417 14th Pl. W., Bothell, WA (US) 98021

(*) Notice: Under 35 U.S.C. 154(b), the term of this patent shall be extended for 0 days.

(21) Appl. No.: 09/302,063

(22) Filed: Apr. 29, 1999

(51) Int. Cl.⁷ .................................................. A61B 8/14
(52) U.S. Cl. .................................................. 600/458
(58) Field of Search .................................. 600/440, 441, 600/443, 458; 367/7

(56) References Cited

U.S. PATENT DOCUMENTS

| 5,255,683 | 10/1993 | Monaghan . |
| 5,694,937 | 12/1997 | Kamiyama . |
| 5,735,281 | 4/1998 | Rafter et al. . |
| 5,740,807 | 4/1998 | Porter . |
| 5,848,968 | * 12/1998 | Takeuchi ........................... 600/458 |
| 5,873,829 | * 2/1999 | Kamiyama et al. ............... 600/458 |

OTHER PUBLICATIONS

Miller, Ultrasonic detection of resonant cavitation bubbles in a flow tube by their second–harmonic emissions, Ultrasonics, Sep. 1981, at pp. 217–224.

Burns et al., Harmonic power mode Doppler using microbubble contrast agents, JEMU, 1994, vol. 16, No. 4, at pp. 132–142, Masson, Paris, 1995.

Burns et al., Harmonic Imaging Principles and Preliminary Results, Angiology, Jul. 1996, vol. 47, No. 7, Pt. 2, at pp. S63–S74, Westminster Publications, Inc. Glen Head, NY.

* cited by examiner

Primary Examiner—Marvin M. Lateef
Assistant Examiner—Ali M. Imam

(57) ABSTRACT

Perfusion of tissue such as the myocardium by a microbubble contrast agent is imaged in realtime by a multiple pulse technique which uses low power transmit pulses which are sufficient to elicit a harmonic response from the microbubbles but are not high enough in power to cause substantial destruction to the microbubbles. In a preferred embodiment the realtime microbubble image sequence is displayed in color, overlaid with a grayscale image of the surrounding tissue in the region being imaged.

16 Claims, 2 Drawing Sheets

REALTIME ULTRASONIC IMAGING OF PERFUSION USING ULTRASONIC CONTRAST AGENTS

This invention relates to methods and apparatus for performing ultrasonic diagnostic imaging and, in particular, to the imaging of perfused tissue in realtime using ultrasonic contrast agents.

Ultrasonic contrast agents are becoming increasingly available to enhance the ultrasonic imaging of bloodflow and tissue perfusion. These contrast agents are generally composed of encapsulated microbubbles of various gases which are highly reflective of ultrasound. When the microbubbles are infused into the body, the bloodflow carrying the microbubbles through blood vessels or the capillary bed of perfused tissue can be delineated by detecting the significant echo reflections from the microbubbles in the bloodstream. Microbubbles have also been found to have another another characteristic which is useful which is that, under certain conditions, the microbubbles will resonate and return ultrasonic echoes at frequencies which are harmonics of the transmit frequency of an insonifying acoustic wave. This means that the echoes from microbubbles can be distinguished or segmented from echoes from other structures on the basis of their higher frequency content. This has led to the desire to enhance the imaging of bloodflow and particularly perfused tissue such as the myocardium with contrast agents, and most desirably to be able to do so in realtime.

There have been several impediments to doing so, however. One is the fragile nature of the microbubbles in the presence of acoustic energy. When insonified with acoustic energy at the higher diagnostic levels, microbubbles have been found to become disrupted and break up or dissolve. Often this disruption is instantaneous in effect, causing the generation of a distinct acoustic signature by the microbubbles. This appreciable return energy can be imaged to great effect as described in U.S. Pat. No. 5,456,257 which uses the energy released by "bursting" microbubbles to image the locations of these microbubble destruction events. But since these events are instantaneous and not repeatable, a drawback of this technique is that only a very few or even only a single image can be acquired at the time of microbubble destruction. A subsequent image at the same location cannot be acquired until the location is reperfused with a new flow of microbubbles.

Faced with this dilemma, a number of techniques have been developed to deal with the problem. These techniques all revolve around the concept of intermittently transmitting ultrasonic energy which disrupts the microbubbles. During the intervening times either low energy transmission or no transmission at all takes place. U.S. Pat. Nos. 5,560,364, 5,740,807, and 5,735,281 all describe variations of this basic premise of acquiring a high energy image of the contrast agent intermittently, while low energy imaging or no imaging is done during the intervening time periods while waiting for the bloodflow to reinfuse the imaged region with a new supply of microbubbles. Such a technique allows imaging of the structure of blood vessels and vasculature in realtime, with periodic filling in of the bloodflow inside those vessels when the high energy contrast agent image is acquired. While the structure of the tissue is shown in realtime, the contrast agent is not.

A second impediment to contrast agent imaging is the contamination of the received microbubble echoes with echoes from tissue. This occurs at the fundamental transmit frequency and at the harmonic frequencies. Harmonic contamination is caused by the development of harmonic components in the transmit wave as it passes through tissue, and the reflection of these tissue harmonic components by the microbubbles in addition to their own harmonic resonant energy. The tissue harmonic signal components should be eliminated from the received signal so that only the harmonic components of the microbubbles are used to form the contrast image.

In accordance with the principles of the present invention, the bloodflow in organs, tissue and vessels is imaged in realtime with the enhancement of a microbubble contrast agent. The ultrasound pulses which are transmitted to scan the imaged area are transmitted at a low power level which is insufficient to cause substantial destruction of the microbubbles yet high enough in power to elicit a harmonic response from the microbubbles. Additionally, at a low power level tissue is not generating a significant harmonic component. Upon reception of the echoes, nonlinear signal components are separated from the linear (fundamental frequency) components, preferably by a multiple pulse inversion technique, and used to create the image. The contrast agent is imaged by processing the nonlinear echo components received from multiple echoes from each sample volume of the imaged bloodflow. The inclusion of tissue harmonic echo components in the processed signals is suppressed by the use of low power, with any residual effects removed by a thresholding technique. In a preferred embodiment the echo signals are filtered to further attenuate fundamental frequency components. The processed signals from the microbubbles are preferably displayed in combination with a structural display of the surrounding tissues and with a distinctive appearance as by display of the microbubble locations in color.

Figure 1:
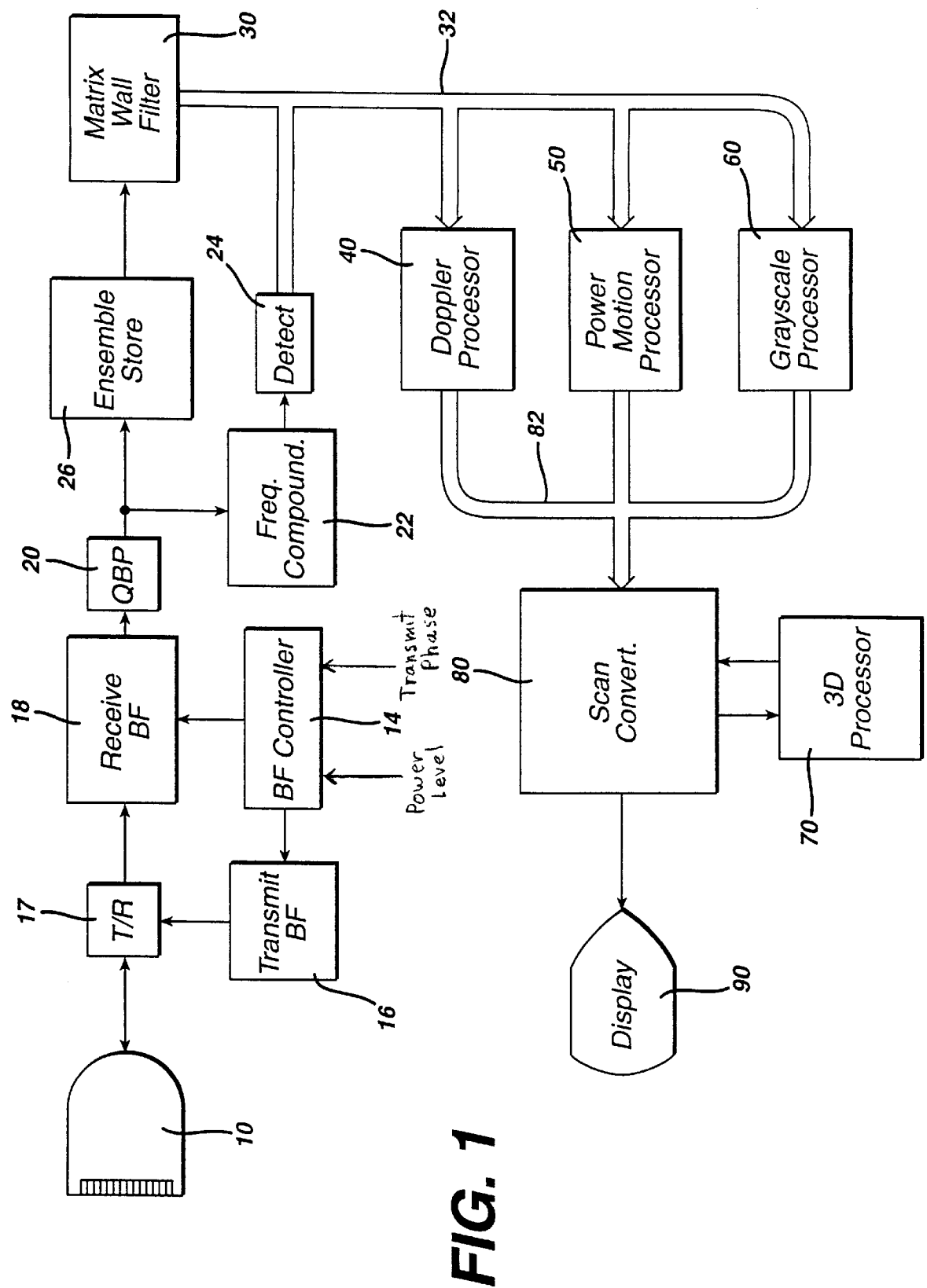
FIG. 1 illustrates in block diagram form an ultrasonic diagnostic imaging system constructed in accordance with the principles of the present invention.

Referring first to FIG. 1, an ultrasonic diagnostic imaging system constructed in accordance with the principles of the present invention is shown in block diagram form. A probe 10 which includes an array transducer 12 transmits ultrasonic energy into the body and receives echoes returned from tissue, cells and flowing substances in the body, including ultrasonic contrast agents when used. The array transducer can be a linear or curved array, and can be operated as a phased array or linear array. Phased array operation is often preferred for cardiology applications. The timing of transmission and reception by the array transducer is synchronized by a beamformer controller 14 which is connected to a transmit beamformer 16 and a receive beamformer 18. The channels of each beamformer are connected to the individual elements of the array transducer so as to separately control the transmission and reception of signals from the individual elements. The transmit beamformer 16, under control of the beamformer controller, determines the time at which each element in the array is actuated to transmit a wave or pulse. This controlled timing of transmission enables the wave transmitted by the entire array to be steered in a given direction, that is, along a predetermined scanline, and to be focused at the desired depth of focus. The beamformer controller 14 is also responsive to a Power Level control signal set by the user which sets the power level of the transmit energy, and is responsive to a Transmit Phase control signal which controls the relative phase or polarity of the transmit pulses. The channels of the two beamformers are coupled to elements of the array by transmit/receive switches 17 which protect the receive beamformer channel inputs from high transmit voltages.

The echoes received by individual transducer elements are coupled to individual channels of the receive beamformer 18 by the transmit/receive switches 17. These input paths may also include preamplifiers to amplify the received echo signals and time gain compensation circuits to compensate for the effects of depth dependent attenuation. When the receive beamformer 18 is a digital beamformer as it is in the preferred embodiment, each channel of the beamformer is preceded by or includes an analog to digital converter. The channels of the beamformer continuously appropriately delay the echoes received by each transducer element from along the scanline so that the signals received from common points (sample volumes) along the scanline are brought into time coincidence. The continual delay variation effects dynamic focusing of the received echo signals along the scanline. The signals at the outputs of the channels are then combined to form a sequence of coherent echo signals.

Receive beamformers also conventionally perform other processing operations such as normalization of signal amplitudes to offset the effects of dynamic aperture changes. The receive beamformer may also be partitioned into two or more groups of channels, each with its own unique delay programming from the beamformer controller, to perform multiline reception. In multiline reception, each group of channels steers and focuses a received beam along its own scanline, thereby forming two or more received scanlines simultaneously. While multiline reception can increase frame rate by acquiring all of the scanlines of one image in less time, it is prone to aberration effects, since not all of the received scanlines are coincident with the transmit aperture.

In one mode of operation, the sequence of coherent echoes received along the scanline are detected, scaled to a range of grayscale values, scanconverted to the desired image format, and displayed, thus forming a B mode image. In the apparatus of FIG. 1, the coherent echoes are demodulated by a quadrature bandpass (QBP) filter 20 into in-phase (I) and quadrature (Q) samples in a predetermined passband. The passband defined by the QBP filter can also roll off fundamental frequency components and unwanted out-of-band signals. For harmonic imaging the passband is located at a band of harmonic frequencies of the fundamental transmit frequency. The I,Q samples can be Doppler processed to determine Doppler power, velocity, acceleration, variance, and the direction of flow or motion, and can also be used to detect the amplitude of the echo signal by the algorithm $(I^2+Q^2)^{1/2}$. For B mode imaging in the embodiment of FIG. 1, the I,Q samples are processed to remove speckle by frequency compounding circuit 22. The echo amplitude is detected by a detector 24 and the detected echo signals are applied to a grayscale processor 60 by way of an echo data bus 32, where the echoes undergo log compression and are grayscale mapped. The grayscale signals are coupled to a scan converter 80 by way of an image data bus 82, where the R-θ scanline data is converted to the desired display format. The scan converted image is displayed on a display 90.

For Doppler imaging the scanline is repetitively scanned over an interval of time to gather a sequence of temporally distinct echoes at each sample volume along the scanline. This temporal echo sequence, called an ensemble, is acquired by a sequence of transmit waves, the repetition frequency of which is called the pulse repetition frequency, or PRF. Each individually transmitted wave or pulse exhibits a nominal frequency which is in the normal r.f. range of diagnostic ultrasound. PRFs are usually in the kilohertz range or lower. The echo ensembles are accumulated in an ensemble store 26 from which completed ensembles are produced for Doppler processing.

The conventional first step in Doppler processing is wall filtering. When imaging or measuring bloodflow in the heart and blood vessels, the relatively low level echoes from blood cells can be overwhelmed by strong echoes reflected by nearby tissue such as a vessel or heart wall. Since the intent of the procedure is to image or measure bloodflow, the tissue echoes are, in this instance, clutter which can be eliminated. The circuitry which eliminates these unwanted signals is called a wall filter, since its basic purpose is to eliminate echoes from the heart and vessel walls. These signals may be discriminated by amplitude, frequency, or a combination of these two characteristics since tissue signals are generally of greater amplitude and lower Doppler frequency than bloodflow signals. A preferred technique for eliminating tissue signals as well as Doppler motion artifacts known as "flash" is shown in U.S. Pat. No. 5,197,477.

The wall filter may also be operated with a reverse characteristic so as to pass tissue Doppler signals to the exclusion of bloodflow Doppler signals. When these signals of the tissue are Doppler processed, images of moving tissue such as the heart muscle and valves can be produced. This imaging technique is known as tissue Doppler imaging.

The filtered Doppler signals, bloodflow or tissue, are applied to a Doppler processor 40 where they are used to perform Doppler estimation of the Doppler phase shift or signal intensity (power Doppler). Conventionally this is done by a Fourier transformation or autocorrelation of the Doppler signal data. A preferred technique is to perform a two dimensional autocorrelation which simultaneously estimates the Doppler phase shift and the reference or center frequency of the Doppler signal. The latter is useful for correction of the effects of depth dependent frequency attenuation in the phase shift estimation. Such a two dimensional Doppler processor is described in U.S. Pat. No. 5,386,830. Since the Doppler frequency or phase shift is proportional to the velocity of the bloodflow or tissue which returned the echoes, the production of a velocity, acceleration or variance estimate is straightforward. In colorflow Doppler the velocities of bloodflow are mapped to a color scale, coupled to the scan converter 80 over the image data bus 82, and overlaid on a grayscale image of the tissue structure containing the bloodflow. In power Doppler imaging the intensity of the Doppler signals is similarly mapped and displayed on a grayscale image. Doppler and grayscale image data can also be processed by 3D processor 70 to form three dimensional image presentations of the bloodflow and/or tissue, as described in U.S. Pat. Nos. 5,474,073 and 5,720,291.

A power motion processor 50 is provided for the power motion imaging mode. The power motion processor receives two or more temporally different echoes from a sample volume and differentiates the signals on an amplitude basis. The differential result is indicative of motion, is scaled to a range of display values and displayed, preferably in color in combination with a B mode structural image. Power motion imaging is described in further detail in U.S. Pat. No. 5,718,229.

In accordance with the principles of the present invention the ultrasonic imaging system of FIG. 1 is used to produce realtime image sequences of a microbubble contrast agent. In the aforementioned '364, '807, and '281 patents, a microbubble contrast agent is imaged by transmitting high power pulses to elicit the strong echoes of microbubble destruction. Since the contrast agent is locally destroyed by the high energy pulses, an intervening time of no pulses or low power pulses is used to allow a reinfusion of new microbubbles into the image area, whereupon the contrast agent can be imaged again. In the technique of the present invention, exactly the opposite approach is taken. A high power pulse or pulses may be initially transmitted to disrupt or destroy the microbubble contrast agent in the region being imaged. Thereafter the microbubbles are imaged in realtime by low power transmit pulses, and the reinfusion of the blood vessel or tissue vasculature is observed in realtime as it progressively occurs over one or more cardiac cycles. The user can thus observe the time required to reperfuse the vasculature of the tissue and/or the number of heart cycles required to reinfuse the tissue with blood containing the contrast agent. Such realtime images can reveal areas of tissue such as the myocardium which do not reperfuse as rapidly as surrounding tissue or do not reperfuse at all, indications of an infarct. The time or number of heart cycles required for reperfusion can also be indicative of arterial obstructions of coronary artery disease.

In order to be able to continually observe the reperfusion of the microbubbles in realtime, it is necessary that the transmit pulses not disrupt or destroy the microbubbles. In accordance with one aspect of the present invention, low energy pulses are used to image the microbubbles in realtime. The energy is high enough to cause the microbubbles to resonate nonlinearly and thus be imaged harmonically, but is not high enough to cause substantial disruption of the microbubbles. "Substantial disruption" is detectable in several ways. When the patient is being steadily infused with the contrast agent and there is a constant flow of microbubbles to the imaged region of the body, the imaged microbubbles should have a substantially constant brightness when fully perfusing the imaged region. If the imaging pulses are interrupted and then resumed, the imaged microbubbles should reappear with substantially the same brightness as they exhibited prior to interruption of imaging. If the contrast agent reappears with a significantly increased brightness upon resumption of imaging, that is an indication that microbubbles are being destroyed because the transmit power level is too high. The power should be reduced to maintain a substantially constant intensity following imaging interruption. This technique of finding the optimal transmit power can be used to determine an optimal transmit power for the specific contrast agent being used in a particular diagnostic procedure.

When the patient is being infused with a short injection of the contrast agent, a large flow or "bolus" of microbubbles will pass through the body. The use of a bolus will produce a wash-in, wash-out effect as the flow of microbubbles builds to a peak at the imaged region, then declines as the greatest density of microbubbles passes out of the region. The realtime imaging of the bolus flow should follow this increase and decline, with the brightness of the imaged microbubbles increasing as the bolus approaches then decreasing after the bolus passes through the region. When there is no substantial disruption of the microbubbles, the brightness or intensity of the realtime image should follow this cycle, becoming increasingly bright then decreasing in intensity. If the buildup and decline of intensity is erratic or there is a decline in intensity during the buildup of the bolus, the power level is too high and should be reduced.

In accordance with another aspect of the present invention, the present inventors have determined that different contrast agents will exhibit different energy levels above which substantial microbubble destruction will occur, depending upon a number of microbubble characteristics. The size of the microbubbles in the contrast agent solution and the shell material used to encapsulate the gas will have a bearing on the fragility of the microbubbles and hence the energy level at which the microbubbles will be destroyed. The present inventors have noted, for instance, that Optison, a contrast agent made by MBI of San Diego, Calif., exhibits substantially no microbubble destruction when imaged in realtime at a mechanical index (MI) of 0.1 or less. The mechanical index of a transmitted ultrasound wave is a measure of the pressure of the transmitted wave. Today's generation of ultrasound systems allows the user to set the transmit MI up to a maximum setting of 1.9 under regulations of the U.S. Food & Drug Administration. The present inventors have discovered that Optison can be continuously imaged in realtime at MI=0.1 or less. When it is desired to destroy the microbubbles in the image plane so that the reinfusion of Optison into the imaged region can be observed in realtime, an image with a higher MI, such as MI=0.9, is transmitted, whereafter the reinfusion of microbubbles can be observed in realtime by continuing to image with transmit pulses at the lower MI.

In accordance with a further aspect of the present invention, imaging of the microbubble contrast agent is enhanced by imaging the harmonic of the microbubble echoes while suppressing tissue harmonic signals, which constitute clutter when performing harmonic contrast imaging. Another reason for using low power transmit pulses, in addition to the need to prevent significant microbubble destruction, is the ability to minimize the generation of tissue harmonic signals. As explained in U.S. Pat. No. 5,879,303, tissue will distort the uniform sinewave of a narrowband ultrasound wave passing through it, causing the wave to acquire harmonic components. These harmonic components will build in proportion to the amplitude of the transmit pulse and the distance traveled through the tissue. The present inventors have noted that as the transmit power of the imaging pulses is reduced, tissue harmonic components drop off faster than the harmonic components of microbubbles. Tissue harmonics can therefore be optimally reduced by transmitting lower energy (amplitude) pulses, consistent with the desire to minimize microbubble destruction but possibly contrary to the need to sufficiently stimulate microbubbles into harmonic resonance. Hence, for a given microbubble contrast agent, a balance of these three considerations must be struck around a transmit power level which produces a significant harmonic response from microbubbles but still maintains a reduced tissue harmonic response.

In addition to using a low power level which reduces the generation of tissue harmonic signals, a preferred embodiment of the present invention removes tissue harmonic signals by a thresholding technique. Referring to the Doppler frequency spectrum of FIG. 2, the spectral band 100 illustrates the location of signals from stationary and slowly moving tissue located about the Nyquist limit of the Doppler PRF when linear and nonlinear signal components are separated by the pulse inversion technique. Around the center of the spectrum is a spectral band 102 containing harmonic components from microbubbles. At the same location is a spectral band 104 containing tissue harmonic components. When low energy transmit pulses are used for imaging the tissue harmonic components will be of a lower amplitude than the microbubble harmonic components. The tissue harmonic components may therefore be removed by passing signals above a threshold Th. shown by the dashed line 106, which will eliminate the tissue harmonic signals below the threshold while passing those above the threshold. The thresholding operation can be performed after wall filtering.

In a preferred embodiment of the present invention, the microbubbles are imaged by a multiple pulse technique. In a multiple pulse technique, each sample volume in the image where microbubbles are imaged is interrogated by two or more pulses, the echoes from which are combined during processing. In addition to the expected signal to noise improvement of using two echoes from a sample volume, the multiple pulse technique provides several other advantages. One is the ability to separate the linear (fundamental frequency) and nonlinear (harmonic frequency) echo components by pulse inversion processing. Pulse inversion is a technique in which multiple pulses are transmitted with differing phases or polarities from pulse to pulse. The received echoes from the multiple pulses are combined, resulting in the cancellation of the linear signal components and reinforcement of the nonlinear components when the multiple echoes are additively combined. Thus, the nonlinear (second harmonic) signal components are separated from the linear (fundamental) components. In a preferred embodiment the multiple pulses are 180° out of phase with each other or of opposite polarity (+ or −) from pulse to pulse. When the pulse inversion separated harmonic signals are Doppler processed, it is preferred to use a pulse inversion Doppler technique as described in U.S. patent [application Ser. No. 09/156,097 filed Sep. 17, 1998]. In pulse inversion Doppler the combining of the signal components of the ensemble by wall filtering or Doppler processing will result in the separation of the nonlinear echo components.

A second advantage of a multiple pulse technique is the reduction of the undesired effects of tissue motion. The microbubble contrast agent being imaged flows through tissue, blood vessels, and the heart by the contractions of the heart every cardiac cycle. The varying pressure of the blood flow causes the vessel walls and perfused tissue to move in response to these pressure changes. The motion is particularly acute when imaging the myocardium of the beating heart. This tissue motion will cause the spectral band 100 of tissue echoes in FIG. 2 to broaden and/or move closer to the microbubble spectrum 102, and can result in less cancellation of the tissue components. With multiple pulses, greater length echo ensembles can be processed at each sample volume, enabling the use of longer filters with greater numbers of coefficients and a filter characteristic which rolls off significantly prior to the passband of undesired tissue motion.

A further advantage of a multiple pulse technique is the ability to detect and image the motion of the microbubbles, which may be done by the Doppler processor 40 or the power motion processor 50 in FIG. 1. When Doppler imaging is used the multiple echoes from the sample volumes are used as a pulse ensemble which is processed to detect the Doppler shift of the flowing microbubbles. The detected Doppler signal is preferably displayed in a color display of the microbubbles. When power motion imaging is used the multiple pulses from the sample volumes are differentiated and the differential signals displayed, preferably in color.

The wall filter 30 is preferably implemented as a matrix filter of the form $$\begin{bmatrix} y_1 \\ y_2 \\ y_3 \\ \vdots \\ y_n \end{bmatrix} = \begin{bmatrix} w_{11} \ldots w_{1n} \\ w_{21} \ldots w_{2n} \\ w_{31} \ldots w_{3n} \\ \vdots \\ w_{n1} \ldots w_{nn} \end{bmatrix} \cdot \begin{bmatrix} x_1 \\ x_2 \\ x_3 \\ \vdots \\ x_n \end{bmatrix}$$

where the echo samples are $x_1 \ldots x_n$, and $w_{11} \ldots w_{nn}$ are weighting coefficients. When a two pulse ensemble is used the preferable weights for the two signals are 0.5 and 0.5. When a three pulse ensemble is used it is preferable to uses weights of 0.25, 0.5, and 0.25. With the use of pulse inversion imaging the received echoes will have alternating phases or polarities, and be of the form $+x_1$, $-x_2$, and $+x_3$. The combining of two +x echoes weighted at 0.25 each with one −x echo weighted at 0.5 will result in separation of the second harmonic components of these signals as well as imposing a filter characteristic which will attenuate fundamental frequencies. Higher order filters will provide better control of the filter characteristic, such as a sharper filter response cutoff than can be attained with lower order filters.

Figure 2:
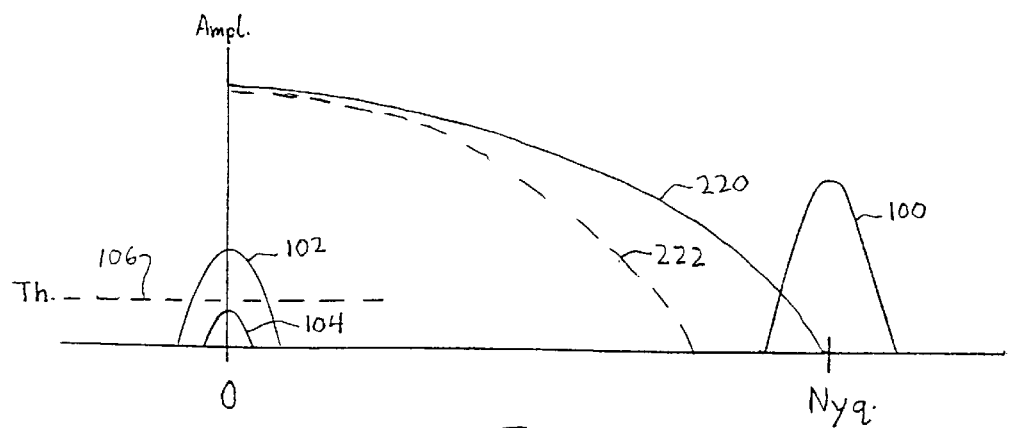
FIG. 2 illustrates a Doppler domain spectrum showing different components of a received echo signal during contrast agent imaging.

When a three pulse technique is utilized, an ensemble of three echo signals is produced for each sample volume. The filter characteristic 220 of a two pulse embodiment is shown in FIG. 2, as well as the filter characteristic 222 of a three pulse embodiment. As expected, the three pulse embodiment results in a greater rolloff and attenuation of the fundamental tissue components. Even greater rolloff can be obtained with four and five pulse embodiments.

In a preferred embodiment the realtime imaging of the microbubble contrast agent comprises a realtime sequence of images with the contrast agent displayed in color by a multiple pulse technique, which overlays or is combined with a grayscale display of the surrounding tissue structure, e.g., blood vessel walls or the myocardium. The grayscale display delineates the tissue structure in which the microbubbles are flowing or perfusing, and is displayed in realtime concurrently with the realtime color display of the contrast agent. Typically B mode pulses which produce the grayscale structure are time interleaved with the multiple pulse sequences used to acquire the ensembles of echoes for the sample volumes where the contrast agent is being observed, and both types of pulses are at a low power level which results in substantially no destruction of the contrast agent.

In one particularly advantageous use of the present invention, one or two high power pulses are transmitted along each scanline of the image field to cause substantial destruction of microbubbles in the region being imaged. Higher power levels will result in a thicker slice of microbubble destruction, correspondingly resulting in a longer time to complete reperfusion. The ultrasound system then begins realtime harmonic imaging of the microbubbles with a low power multiple pulse technique, and the detected microbubbles are overlaid in color on realtime grayscale image frames. As the microbubbles begin to reperfuse the imaged region, the user can observe the buildup of microbubbles in color in realtime as reperfusion takes place over one or more cardiac cycles. The technique can be gated to the cardiac cycle if desired, so that the microbubble destruction event takes place at a predetermined point in the heart cycle such as end diastole. In such a procedure using Optison, the high power microbubble destruction pulses had an MI>0.7, preferably MI≧0.9, the realtime imaging pulses had an MI<0.2, and preferably MI≦0.1, the PRF was set at 1500 Hz, and the frame rate was set at 15 Hz.

An effective contrast ultrasound technique is one that images the contrast agent bubbles effectively while suppressing the tissue. One way of doing this is by insonifying the bubbles with high amplitude ultrasound repeatedly (within a frame) to destroy these bubbles and thus generate a strong Doppler signal. Since this method destroys a large amount of bubbles, intermittent imaging is utilized (ECG triggering or other predetermined delays) to allow time for the organ being imaged to reperfuse.

Another bubble acoustic signature (other than destruction) is the increased backscattered signal in both the fundamental and harmonic components. Tissue also gives strong backscattered signals at the fundamental and second harmonic components. The backscattered signals at the second harmonic component however are highly dependent upon the amplitude of the transmitted acoustic wave. Thus, at low amplitudes not much appreciable second harmonic component from tissue is present while the contrast bubbles that are more nonlinear than tissue still generate detectable second harmonic components.

Figure 3:
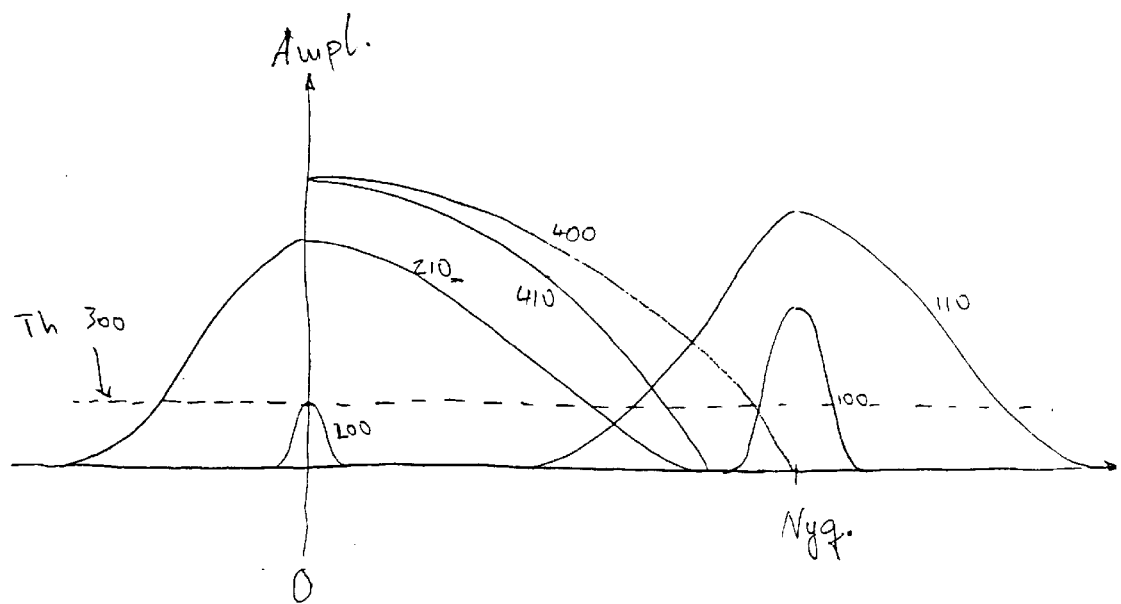
FIG. 3 illustrates a Doppler domain spectrum showing different spectral bands before and after contrast agent infusion.

In a preferred embodiment of our invention we insonify the contrast microbubbles with a small amplitude signal (MI<<1) to limit second harmonic generation in the tissue but which is high enough to generate second harmonic signals from microbubbles. The small amplitudes utilized also result in very limited bubble destruction and real time imaging is possible since we do not have to wait a certain time between frames for organ reperfusion. This method is further improved by utilizing the pulse inversion method where a series of pulses that are 180 degrees out of phase from each other (inverted) are transmitted. With the pulse inversion technique the fundamental and second harmonic components are separated as shown in FIG. 3. Band 200 is the tissue second harmonic component and band 100 is the fundamental before any contrast bubbles are injected. After the contrast injection bands 200 and 100 change to 210 and 110 respectively. The Doppler data $x_n$ are multiplied with a wall filter matrix as shown above. The effect of the wall filter is shown in FIG. 3 by lines 400 and 410, which represent characteristics produced by filters of different length. In the present invention we further eliminate any baseline (prior to contrast injection) signals by thresholding as shown with threshold line 300. Different wall filters are designed for eliminating or mixing various amounts of fundamental with second harmonic signals. In the preferred embodiment, tissue motion, which is most prevalent in the fundamental frequency signals, is eliminated by the wall filter characteristic.

In summary the pulse inversion scheme (transmitting alternately inverted pulses, then combining the echoes) separates the linear from the nonlinear components, the wall filter selectively rejects motion at the fundamental frequency, and finally a thresholding scheme is applied to eliminate all signals in a baseline image.

What is claimed is:

1. A method for imaging an ultrasonic microbubble contrast agent in a region of the body in realtime comprising the steps of:

transmitting pulses and receiving echoes to produce a grayscale image of tissue in the region of the body being imaged;

transmitting time interleaved pulses and receiving multiple temporally discrete echoes from each of the sample volumes in the region where microbubbles are being imaged;

separating harmonic components of said multiple echoes from said sample volumes and producing display signals of said microbubbles of said sample volumes from the harmonic components of said multiple echoes of said sample volumes; and displaying a realtime image sequence of said grayscale tissue signals combined or overlaid with said microbubble display signals in a distinguishing color, wherein said transmitted pulses for said realtime image sequence are at a power which is low enough to cause no substantial microbubble destruction in said imaged region but at a power which is sufficiently high enough to cause a detectable harmonic response by said microbubbles.

2. The method of claim 1, wherein said multiple pulses used to image said microbubbles are produced in a format suitable for pulse inversion separation of harmonic signals from said microbubbles.

3. The method of claim 1, wherein said region of the body is the heart, liver, kidney or cranium.

4. The method of claim 3, wherein said region of the body is the myocardium, wherein said realtime image sequence shows the perfusion of the myocardium in realtime.

5. The method of claim 1, further comprising the step of separating harmonic microbubble signal components from tissue harmonic signal components by a thresholding technique.

6. The method of claim 1, wherein said step of displaying displays a realtime image sequence of microbubbles at a frame rate of at least 15 frames per second.

7. The method of claim 1, wherein said step of producing display signals of said microbubbles comprises producing display signals by the Doppler technique.

8. The method of claim 7, wherein said step of producing display signals of said microbubbles further comprises producing display signals by the pulse inversion Doppler technique.

9. The method of claim 1, wherein said step of producing display signals of said microbubbles comprises producing display signals by the technique of power motion imaging.

10. A method for observing tissue perfusion by use of an ultrasonic microbubble contrast agent continuously in realtime over one or more cardiac cycles comprising the steps of:

repetitively transmitting pulses and receiving echoes to produce a grayscale image of said tissue;

repetitively transmitting time interleaved pulses and receiving multiple temporally discrete echoes from each of the sample volumes in the tissue where microbubbles are being imaged;

separating harmonic components of said multiple echoes from said sample volumes and producing display signals of said microbubbles of said sample volumes from the harmonic components of said multiple echoes of said sample volumes; and displaying a realtime image sequence of said grayscale tissue signals combined or overlaid with said microbubble display signals in a distinguishing color, wherein said transmitted pulses for said realtime image sequence are at a power which is low enough to cause no substantial microbubble destruction in said imaged region but at a power which is sufficiently high enough to cause a detectable harmonic response by said microbubbles.

11. The method of claim 10, wherein said perfused tissue is the myocardium, liver, kidney or cranium.

12. The method of claim 11, further comprising the initial step of transmitting one or more high power pulses along each scanline of said image to cause substantial disruption to the microbubbles in the region of said tissue being imaged.

13. The method of claim 11, wherein said step of repetitively transmitting time interleaved pulses comprises transmitting pulses of alternating phase or polarity, and wherein said step of separating harmonic components of said multiple echoes from said sample volumes comprises separating harmonic components by pulse inversion processing of the echoes received at said sample volumes in response to the transmission of pulses of alternating phase or polarity.

14. The method of claim 13, wherein said step of separating harmonic components of said multiple echoes further comprises Doppler processing ensembles of harmonic echoes from each sample volume which have been separated from linear signal components by the process of pulse inversion.

15. A method for observing tissue perfusion by use of an ultrasonic microbubble contrast agent continuously in realtime over one or more cardiac cycles comprising the steps of:

repetitively transmitting pulses and receiving echoes to produce a grayscale image of said tissue;

repetitively transmitting time interleaved pulses and receiving multiple temporally discrete echoes from each of the sample volumes in the tissue where microbubbles are being imaged;

separating harmonic components of said multiple echoes from said sample volumes and producing display signals of said microbubbles of said sample volumes from the harmonic components of said multiple echoes of said sample volumes;

displaying a realtime image sequence of said grayscale tissue signals combined or overlaid with said microbubble display signals in a distinguishing color; and optimizing the transmitted pulse energy for said realtime image sequence to a power which is low enough to cause no substantial microbubble destruction in said imaged region.

16. The method of claim 15, wherein the step of optimizing comprises setting the transmit power to a level which causes no substantial change in brightness of an imaged microbubble contrast agent under conditions of steady-state perfusion of said imaged region.

* * * * *